United States Patent
Chapuis et al.

(10) Patent No.: US 10,023,514 B2
(45) Date of Patent: Jul. 17, 2018

(54) ODORANTS OF THE VIOLET TYPE

(71) Applicant: FIRMENICH SA, Geneva (CH)

(72) Inventors: Christian Chapuis, Geneva (CH); Hervé Mosimann, Geneva (CH)

(73) Assignee: Firmenich SA, Geneva (CH)

( * ) Notice: Subject to any disclaimer, the term of this patent is extended or adjusted under 35 U.S.C. 154(b) by 334 days.

(21) Appl. No.: 14/650,140

(22) PCT Filed: Nov. 25, 2013

(86) PCT No.: PCT/EP2013/074593
§ 371 (c)(1),
(2) Date: Jun. 5, 2015

(87) PCT Pub. No.: WO2014/086608
PCT Pub. Date: Jun. 12, 2014

(65) Prior Publication Data
US 2015/0315516 A1    Nov. 5, 2015

(30) Foreign Application Priority Data

Dec. 5, 2012   (EP) ..................... 12195579

(51) Int. Cl.
| | | |
|---|---|---|
| A61Q 5/10 | (2006.01) |
| C07C 11/22 | (2006.01) |
| A61Q 13/00 | (2006.01) |
| A61K 8/31 | (2006.01) |
| A61Q 5/06 | (2006.01) |
| A61Q 5/02 | (2006.01) |
| A61Q 9/02 | (2006.01) |
| A61Q 19/00 | (2006.01) |
| A61Q 15/00 | (2006.01) |
| C07C 11/28 | (2006.01) |
| C11B 9/00 | (2006.01) |
| C07C 43/14 | (2006.01) |
| C07C 33/048 | (2006.01) |
| C11D 3/20 | (2006.01) |
| C11D 3/50 | (2006.01) |
| A61K 8/33 | (2006.01) |
| A61K 8/37 | (2006.01) |
| C07C 57/00 | (2006.01) |
| C07C 69/145 | (2006.01) |
| C07C 69/606 | (2006.01) |
| C11D 3/16 | (2006.01) |

(52) U.S. Cl.
CPC .............. *C07C 43/14* (2013.01); *A61K 8/33* (2013.01); *A61K 8/37* (2013.01); *A61Q 5/06* (2013.01); *A61Q 13/00* (2013.01); *A61Q 15/00* (2013.01); *A61Q 19/00* (2013.01); *A61Q 19/002* (2013.01); *C07C 33/048* (2013.01); *C07C 57/00* (2013.01); *C07C 69/145* (2013.01); *C07C 69/606* (2013.01); *C11B 9/003* (2013.01); *C11B 9/0015* (2013.01); *C11B 9/0019* (2013.01); *C11D 3/164* (2013.01); *C11D 3/2068* (2013.01); *C11D 3/2093* (2013.01); *C11D 3/50* (2013.01); *A61K 2800/10* (2013.01)

(58) Field of Classification Search
CPC ........... C11D 3/184; C11D 3/50; C11D 3/001; C11D 3/164; C11B 9/0007
See application file for complete search history.

(56) References Cited

U.S. PATENT DOCUMENTS 5,538,943 A   7/1996 Naef et al.

FOREIGN PATENT DOCUMENTS

| EP | 694804 | 1/1996 | |
|---|---|---|---|
| EP | 1784374 | 3/2008 | |
| WO | WO-2011143242 A2 * | 11/2011 | ............... A61K 8/25 |

OTHER PUBLICATIONS

Dzhemilev et al., Russ Chem Bull ,35: 397. https://doi.org/10.1007/BF00952934) Preview only (Year: 1986).*
STN CASREACT index of reactions disclosed in Dzhemilev et al. downloaded Nov. 14 (Year: 2017).*
International Search Report and Written Opinion, application PCT/EP2013/074593, dated Dec. 20, 2013.
Dilon et al., J. Org. Chem., 1996, 61, 5617-5625.
Peterson et al., J. Am. Chem. Soc., 1966, 88, 4990-4996.
Pirrung et al., Tetrahedron, vol. 50, n° 43, 1994, 12415-12442.
Rodriguez et al., Tetrah. Letters, vol. 53, 2012, 4169-4172.
Scarpa et al, Helv. Chim. Acta, 1966, 49, 858 (German language).
Sevin et al., Bull. Soc. Chim. Fr, 1974, n° 5-6, 913-917 (French language).
Zakharkin et al., Bull. Acad. Sci. USSR, Div. Chem., 1983, 32, 2160-2162.

* cited by examiner

*Primary Examiner* — Bethany P Barham
*Assistant Examiner* — Lisbeth C. Robinson
(74) *Attorney, Agent, or Firm* — Winston & Strawn LLP

(57) ABSTRACT

The present invention relates to the use as perfuming ingredient, in particular to confer odor notes of the violet, violet leaves type, of a compound of formula (I), wherein n represents 1 or 2, A represents $CH_2$ or CO; and R represents a $C_{1-4}$ alkyl or alkenyl group or a $C_3$ cycloalkyl group, or when A is a $CH_2$ group R may also represent a $C_{1-3}$ acyl group. Moreover, following what is mentioned herein, the present invention comprises the invention's compound as part of a perfuming composition or of a perfuming consumer product.

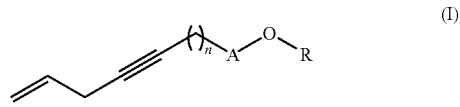

(I)

18 Claims, No Drawings

ODORANTS OF THE VIOLET TYPE

TECHNICAL FIELD

The present invention relates to the field of perfumery. More particularly, it concerns the use as perfuming ingredient of a compound of formula (I), as defined below, in particular to confer odor notes of the violet, violet leaves type. Moreover, following what is mentioned herein, the present invention comprises the invention's compound as part of a perfuming composition or of a perfuming consumer product.

PRIOR ART

The perfumery industry is always searching for new ingredients allowing new possibilities in the accord generation and also rendering the formulation easier and safer. This is also valid for the family of the violet odorant, an important class of ingredients.

Although several compounds of formula (I) have been described in the prior art, in general as simple chemicals, none of the invention's compounds has been described as having organoleptic properties, and furthermore none has been suggested as odorant ingredient.

From a structural point of view, the closest known perfuming ingredients are the ones disclosed in EP 1784374, such as 7-propoxy-1,3-heptadien-5-yne, having also an odor type of the same olfactive family as that of the present invention's compounds. However, said prior art compounds possess a chemical structure quite different, by having an additional ethylene group and by being a fully conjugated compound. By no mean said prior art document suggest the organoleptic properties of the present invention's compounds.

Alternatively, another structurally related perfuming ingredient is 1,3-undecadien-5-yne disclosed in EP 694604 as having a floral, green galbanum odor, which is an odor type of the same olfactive family as that of the present invention's compounds. However, said prior art compound possesses a chemical structure quite different for the same reason as for the previous prior art document plus they do not comprise an ether functional group. By no mean said prior art document suggests the organoleptic properties of the present invention's compounds.

DESCRIPTION OF THE INVENTION

We have now surprisingly discovered that a compound of formula

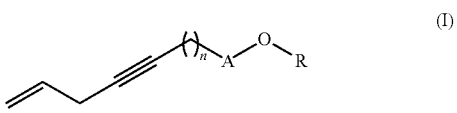

wherein n represents 1 or 2;

A represents $CH_2$ or CO; and

R represents a $C_{1-4}$ alkyl or alkenyl group or a $C_3$ cycloalkyl group, or when A is a $CH_2$ group R may also represent a $C_{1-3}$ acyl group;

can be used as perfuming ingredient, for instance to impart odor notes of the violet, violet leaves type.

According to a particular embodiment of the invention, said compound (I) is a $C_9$-$C_{12}$ compound, or even a $C_{10}$-$C_{12}$ compound.

According to any one of the above embodiments of the invention, said compound (I) is a compound of formula

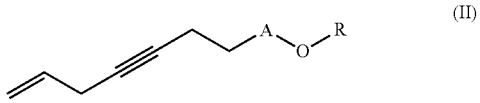

wherein A represents $CH_2$ or CO and R represents a $C_{1-4}$ alkyl or alkenyl group.

The compounds of formula (I), which are as such also an aspect of the present invention, are also new compounds at the exception of methyl oct-7-en-4-ynoate (disclosed in Tet. Letters, 2012, 53, 4169 as chemical intermediate) and of 7-ethoxyhept-1-en-4-yne (disclosed in CA 106:50273 as chemical intermediate).

As specific examples of the invention's compounds, one may cite, as non-limiting example, 8-propoxyoct-1-en-4-yne which is characterized by a complex odor comprising violet leaves, green, fruity-pear and watery notes. The overall odor reminds of the one of a mixture of some well known perfumery ingredients such as (Z)-3-hexen-1-yl isobutyrate, 3-methyl-2-hexenyl acetate and (Z)-3-hexenyl (Z)-3-hexenoate. An appreciated specificity of this compound is a lack of bottom notes of the gas type, which are very frequent in ingredients having violet leaves notes.

As other specific, but non-limiting, examples of the invention's compounds, one may cite the following ones in Table 1:

TABLE 1

Invention's compounds and their odor properties

| Compound structure and name | Odor notes |
|---|---|
| 8-ethoxyoct-1-en-4-yne | Violet, green, galbanum, gas odor notes |
| 8-methoxyoct-1-en-4-yne | Violet, green, galbanum, at bottom gas, acetylene odor notes |

TABLE 1-continued

Invention's compounds and their odor properties

| Compound structure and name | Odor notes |
|---|---|
| 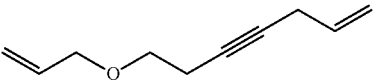<br>7-(allyloxy)hept-1-en-4-yne | Violet leaves, at bottom gas, myroxyde, odor notes |
| 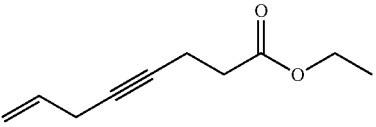<br>ethyl 7-octen-4-ynoate | Violet leaves, fruity, vanillic, odor notes |
| 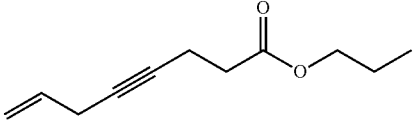<br>propyl 7-octen-4-ynoate | Violet, green, sweet, odor notes |
| 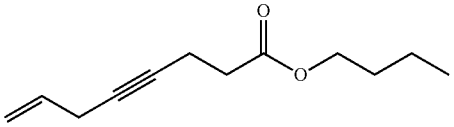<br>butyl 7-octen-4-ynoate | Violet odor notes |
| 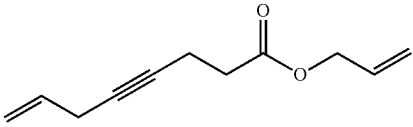<br>allyl 7-octen-4-ynoate | Nice violet leaves odor notes |
| 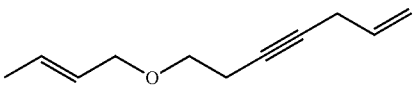<br>7-(but-2-enyloxy)hept-1-en-4-yne | Nice violet, oxadiene, coriander, fruity, pineapple odor notes |
| 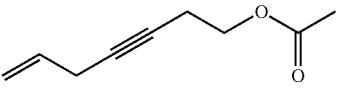<br>hept-6-en-3-ynyl acetate | Violet leaves, gas, green, alliaceous, odor notes |

According to a particular embodiment of the invention, the compounds of formula (I) are 8-propoxyoct-1-en-4-yne, 8-methoxyoct-1-en-4-yne or 7-(allyloxy)hept-1-en-4-yne.

When the odor of the invention's compounds, in particular those of formula (II), is compared with that of the prior art compound of EP 1784374 (in particular 7-propoxy-1,3-heptadien-5-yne), then the invention's compounds distinguish themselves by having a green character which is in the direction of a green-fruity like note while the prior art compounds do have a green character more in the purely violet leave. The present invention's compounds do have an olfactive profile more complex and versatile than the one of the prior art compounds.

As mentioned above, the invention concerns the use of a compound of formula (I) as perfuming ingredient. In other words, it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing a compound (I) and which can be advantageously employed in perfumery industry.

Said compositions, which in fact can be advantageously employed as perfuming ingredients, are also an object of the present invention.

Therefore, another object of the present invention is a perfuming composition comprising:
i) as perfuming ingredient, at least one invention's compound as defined above;

ii) at least one ingredient selected from the group consisting of a perfumery carrier and a perfumery base; and iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carriers one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilizers, thickening and gelling agents in foods, Volume 2 of the series of Food Chemistry, Food Quality, Behr's Verlag GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation technique.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

Furthermore, the invention's compound can also be advantageously used in all the fields of modern perfumery, i.e. fine or functional perfumery, to positively impart or modify the odor of a consumer product into which said compound (I) is added. Consequently, a perfuming consumer product which comprises:

i) as perfuming ingredient, at least one compound of formula (I), as defined above; and ii) a perfumery consumer base;

is also an object of the present invention.

The invention's compound can be added as such or as part of an invention's perfuming composition.

For the sake of clarity, it has to be mentioned that, by "perfuming consumer product" it is meant a consumer product which is expected to deliver at least a perfuming effect, in other words it is a perfumed consumer product. For the sake of clarity, it has to be mentioned that, by "perfumery consumer base" we mean here the functional formulation, as well as optionally additional benefit agents, corresponding to a consumer product which is compatible with perfuming ingredients and is expected to deliver a pleasant odor to the surface to which it is applied (e.g. skin, hair, textile, or home surface). In other words, a perfuming consumer product according to the invention comprises the functional formulation, as well as optionally additional benefit agents, corresponding to the desired consumer product, e.g. a detergent or an air freshener, and an olfactive effective amount of at least one invention's compound.

The nature and type of the constituents of the perfumery consumer base do not warrant a more detailed description here, which in any case would not be exhaustive, the skilled person being able to select them on the basis of his general knowledge and according to the nature and the desired effect of said product.

Non-limiting examples of suitable perfumery consumer base can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer product bases may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.01% to 5% by weight, or even more, of the compounds of the invention based on the weight of the composition into which they are incorporated. Concentrations lower than these, such as in the order of 0.001% to 1% by weight, can be used when these compounds are incorporated into perfumed articles, percentage being relative to the weight of the article.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

Synthesis of Compounds of Formula (I)

General Procedure for Allylation

A solution of bromoethane (43.6 g, 400 mmol) in $Et_2O$ (280 ml) was added dropwise to a suspension of Mg (9.6 g, 400 mmol) in $Et_2O$ (140 ml). After 3 hours a solution of alkyne (360 mmol) in $Et_2O$ (140 ml) was added dropwise (T<20° C.). After 90 minutes at reflux, CuCl (1.8 g, 18.2 mmol) was added to the cold reaction mixture and after 15 minutes a solution of allyl bromide (48.4 g, 400 mmol) in $Et_2O$ (140 ml) was added dropwise. After 18 hours at reflux, the cold reaction mixture was poured onto 10% aqueous HCl (320 ml) at 0° C. The aqueous phase was extracted with $Et_2O$, then the organic phase was washed with $H_2O$, dried ($MgSO_4$), concentrated and distilled.

8-propoxyoct-1-en-4-yne

Obtained in 88% yield from 5-propoxypent-1-yne (L. I. Zakharkin, I. M. Churilova, *Bull. Acad. Sci. USSR, Div. Chem. Sci.* 1983, 32, 2160) according to the general procedure. Bp: 90°/1 mbar.
IR: 2934, 2858, 1642, 1421, 1366, 1284, 1195, 1115, 1057, 989, 913.
$^1$H-NMR: 0.92 (t, J=7, 3H); 1.54-1.65 (m, 2H); 1.77 (quint, J=7, 2H); 2.27-2.32 (m, 2H); 2.92-2.95 (m, 2H); 3.38 (t, J=7, 2H); 3.50 (t, J=7, 2H); 5.09 (dq, J=2, 9, 1H); 5.31 (dq, J=2, 18, 1H); 5.77-5.87 (m, 1H).
$^{13}$C-NMR: 133.4 (c); 115.6 (t); 82.2 (s); 76.7 (s); 72.6 (t); 69.3 (t); 29.2 (t); 23.1 (t); 22.9 (t); 15.6 (t); 10.6 (q).

8-ethoxyoct-1-en-4-yne

Obtained in 63% yield from 5-ethoxypent-1-yne (J. S. Scarpa et al. *Helv. Chim. Acta* 1966, 49, 858) according to the general procedure. Bp: 60°/1.1 mbar.
IR: 2976, 2932, 2861, 1642, 1421, 1377, 1358, 1329, 1285, 1198, 1108, 990, 913, 866.
$^1$H-NMR: 1.20 (t, J=7, 3H); 1.78 (quint, J=7, 2H); 2.28-2.32 (m, 2H); 2.92-2.97 (m, 2H); 3.48 (t, J=7, 2H); 3.50 (q, J=7, 2H); 5.09 (dq, J=2, 11, 1H); 5.32 (dq, J=2, 16, 1H); 5.79-5.88 (m, 1H).
$^{13}$C-NMR: 133.4 (d); 115.6 (t); 82.2 (s); 76.8 (s); 69.2 (t); 66.2 (t); 29.2 (t); 23.1 (t); 15.6 (t); 15.2 (q).

8-methoxyoct-1-ene-4-yne

Obtained in 60% yield from 5-methoxypent-1-yne (P. E. Peterson et al. *J. Am. Chem. Soc.* 1966, 88, 4990) according to the general procedure. Bp: 60°/1.3 mbar.
IR: 2924, 2872, 1641, 1421, 1387, 1329, 1285, 1214, 1172, 1117, 1076, 1022, 990, 914.
$^1$H-NMR: 1.78 (quint, J=7, 2H); 2.28-2.32 (m, 2H); 2.92-2.97 (m, 2H); 3.34 (s, 3H); 3.48 (t, J=7, 2H); 5.09 (dq, J=2, 11, 1H); 5.32 (dq, J=2, 16, 1H); 5.78-5.88 (m, 1H).
$^{13}$C-NMR: 133.3 (d); 115.6 (t); 82.0 (s); 76.9 (s); 71.4 (t); 58.6 (q); 29.0 (t); 23.1 (t); 15.5 (t).

7-(allyloxy)hept-1-en-4-yne

Obtained in 34% yield from 4-(allyloxy)-but-1-yne (D. Dilon et al. *J. Org. Chem.* 1996, 61, 5617) according to the general procedure. Bp: 80°/0.15 mbar.
IR: 3082, 2861, 1642, 1420, 1348, 1285, 1099, 990, 915.
$^1$H-NMR: 2.49 (dq, J=7, 5, 2H); 2.92-2.96 (m, 2H); 3.56 (t, J=7, 2H); 4.02 (dt, J=1, 7, 2H); 5.08 (dq, J=2, 11, 1H); 5.18 (dq, J=2, 11, 1H); 5.28 (dq, J=2, 16, 1H); 5.32 (dq, J=2, 16, 1H). 5.76-5.97 (m, 2H).
$^{13}$C-NMR: 134.7 (d); 133.1 (d); 117.1 (t); 115.8 (t); 79.3 (s); 77.8 (s); 71.9 (t); 68.8 (t); 23.1 (t); 20.2 (t).

Ethyl 7-octen-4-ynoate

This compound was obtained by the procedure described by A. Sevin, W. Chodkiewicz, P. Cadiot, in *Bull. Soc. Chim. Fr.* 1974, 913, starting from ethyl 4-pentynoate and allyl bromide. The crude product was distilled through a column filled with glass rings (eb: 91-92° C./8.5 mbar) affording ethyl 7-octen-4-ynoate as a colorless liquid.

$^1$H-NMR: 1.26 (t, $^3$J=7.1, 3H, Et); 2.51 (s, 4H, H—C (2,3)); 2.91 (m, 2H, H—C (6)); 4.15 (q, $^3$J=7.1, 2H, Et); 5.08 (ddd, $^3$J=10.0, $^4$J=3.5, $^2$J=1.9, 1H, H—C (8)); 5.29 (ddd, $^3$J=16.9, $^4$J=3.8, $^2$J=1.9, 1H, H—C (8)); 5.79 (m, 1H, H—C (7)).

$^{13}$C-NMR: 14.3 (q, Et); 14.9 (t, C (3)); 23.1 (t, C (6)); 34.1 (t, C (2)); 60.5 (t, Et); 77.5 (s, C (5)); 80.8 (s, C (4)); 115.7 (t, C (8)); 133.2 (d, C (7)); 172.0 (s, C (1)).

Allyl 7-octen-4-ynoate

A mixture of ethyl 7-octen-4-ynoate (50.0 g), allyl alcohol (86.4 g) and dioctyltin oxide (2.5 g) was heated up to 110° C. Ethanol was distilled as it was formed through a Widmer column increasing slowly the temperature to 145° C. The crude product (66.5 g) was distilled through a short Vigreux column (eb: 61° C./0.5 mbar) affording 50.8 g of allyl 7-octen-4-ynoate as a colorless liquid.

$^1$H-NMR: 2.5-2.6 (m, 4H); 2.90-2.93 (m, 2H); 4.60 (d, J=5.7, 2H); 5.08 (dq, J=1.5, 10, 1H); 5.23 (dq, J=1.5, 10.5, 1H); 5.28 (dq, J=1.5, 14, 1H); 5.33 (dq, J=1.5, 13.8, 1H); 5.75-5.84 (m, 1H); 5.86-5.97 (m, 1H).

$^{13}$C-NMR: 14.8 (t, C (3)); 23.0 (t, C (6)); 34.0 (t, C (2)); 65.2 (t, allyl); 77.6 (s, C (5)); 80.7 (s, C (4)); 115.7 (t, C (8)); 118.2 (t, allyl); 132.2 (d, allyl); 133.0 (d, C (7)); 171.8 (s, C (1)).

Propyl 7-octen-4-ynoate

Same procedure as above, using propyl alcohol instead of allyl alcohol. The crude product (64.8 g) was distilled through a short Vigreux column (eb: 60° C./0.5 mbar) affording 47.8 g of propyl 7-octen-4-ynoate as a colorless liquid.

$^1$H-NMR: 0.95 (t, J=7.2, 3H); 1.65 (sext, J=7.2, 2H); 2.52 (s, 4H); 2.91 (dt, J=2.1, 5.2, 2H); 4.06 (t, J=7.2, 2H); 5.08 (dq, J=1.7, 10, 1H); 5.29 (dq, J=1.7, 17, 1H); 5.75-5.84 (m, 1H).

$^{13}$C-NMR: 10.4 (q, propyl); 14.9 (t, C (3)); 22.0 (t, propyl); 23.1 (t, C (6)); 34.1 (t, C (2)); 66.2 (t, propyl); 77.4 (s, C (5)); 80.8 (s, C (4)); 115.7 (t, C (8)); 133.0 (d, C (7)); 172.2 (s, C (1)).

Butyl 7-octen-4-ynoate

Same procedure as above, using butyl alcohol instead of allyl alcohol. The crude product (61.2 g) was distilled through a short Vigreux column (eb: 68° C./0.5 mbar) affording 47.8 g of propyl 7-octen-4-ynoate as a colorless liquid.

$^1$H-NMR: 0.93 (t, J=7.3, 3H); 1.385 (sext, J=7.3, 2H); 1.61 (quint, J=7, 2H); 2.51 (s, 4H); 2.91 (dt, J=1.8, 5, 2H); 4.10 (t, J=6.6, 2H); 5.08 (dq, J=1.7, 10, 1H); 5.29 (dq, J=1.7, 16.9, 1H); 5.75-5.84 (m, 1H).

$^{13}$C-NMR: 13.7 (q, butyl); 14.9 (t, C (3)); 19.2 (t, butyl); 23.1 (t, C (6)); 30.7 (t, butyl); 34.1 (t, C (2)); 64.5 (t, butyl); 77.4 (s, C (5)); 80.8 (s, C (6)); 115.7 (t, C (8)); 133.0 (d, C (7)); 172.2 (s, C (1)).

(E)-7-(but-2-enyloxy)hept-1-en-4-yne

A solution of but-3-yn-1-ol (2.0 g, 28.5 mmol) in THF (20 ml) was added dropwise on a suspension of NaH (55% in min oil, 1.432 g, 32.8 mmol) in THF (30 ml). After 2 h at 20° a solution of (E)-1-chlorobut-2-ene (3.1 g, 34.2 mmol) in THF (20 ml) was added at 25°. After 4 h the reaction mixture was poured onto H$_2$O, and the aqueous phase was extracted with Et$_2$O. The organic phase was washed with brine, dried (Na$_2$SO$_4$), concentrated, then the resulting 1-(but-3-ynyloxy)-but-2-ene (78:22 E/Z) was used crude after bulb-to-bulb distillation, directly for the following allylation according to the general procedure to afford the desired material in 43% yield as a 78:22 E/Z mixture, after purification by CC/SiO$_2$(cyclohexane/AcOEt 97:3).

IR: 3014, 2917, 2857, 1641, 1421, 1360, 1336, 1285, 1101, 1055, 990, 966, 913

$^1$H-NMR: main isomer (E) 1.72 (dd, J=1.1, 5.8, 3H); 2.45-2.51 (m, 2H); 2.92-2.95 (m, 2H); 3.56 (t, J=7, 3H); 3.94 (dt, J=1.5, 6.5, 2H); 5.14 (dq, J=2.3, 17, 1H); 5.31 (dq, J=2.3, 17, 1H); 5.55-5.62 (m, 1H); 5.65-5.75 (m, 1H); 5.75-5.86 (m, 1H).

minor isomer (Z): 1.66 (dd, J=1.0, 6.5, 3H); 2.45-2.51 (m, 2H); 2.92-2.95 (m, 2H); 3.58 (t, J=7.2, 3H); 4.07 (dt, J=1.5, 6.5, 2H); 5.14 (dq, J=2.3, 17, 1H); 5.31 (dq, J=2.3, 17, 1H); 5.55-5.62 (m, 1H); 5.65-5.75 (m, 1H); 5.75-5.86 (m, 1H).

$^{13}$C-NMR: main isomer (E) 133.1 (d); 129.6 (d); 127.5 (d); 115.7 (t); 79.3 (s); 77.7 (s); 71.6 (t); 68.5 (t); 23.2 (t); 20.2 (t); 17.8 (q).

Hept-6-en-3-ynyl acetate

Ac$_2$O (10 ml) was added dropwise to a solution of hept-6-en-3-yn-1-ol (F. O. H. Pirrung, H. Hiemstra, W. N. Speckamp, B. Kaptein, H. E. Schoemaker, *Tetrahedron* 1994, 50, 12415; 2.0 g, 16.7 mmol) in pyridine (10 ml). After 3 h, the reaction mixture was poured onto ice, then extracted with Et$_2$O (3×30 ml). The organic phase was dried (Na$_2$SO$_4$), concentrated, then purified by bulb-to-bulb distillation to afford quantitatively the desired acetate. Bp: 73°/0.3 mbar.

IR: 2963, 1738, 1641, 1422, 1385, 1364, 1233, 1039, 991, 915.

$^1$H-NMR: 2.07 (s, 3H); 2.51-2.56 (m, 2H); 2.92-2.95 (m, 2H); 4.15 (t, J=7, 2H); 5.10 (dq, J=1.8, 17, 1H); 5.31 (dq, J=1.8, 17, 1H); 5.76-5.86 (m, 1H).

$^{13}$C-NMR: 170.8 (s); 132.9 (d); 115.8 (t); 78.4 (s); 78.2 (s); 62.8 (t); 23.0 (t); 20.9 (q); 19.3 (t).

Example 2

Preparation of a Perfuming Composition

A classical perfuming composition, of the floral-violet-powdery type, was prepared by admixing the following ingredients:

| Ingredient | Parts by weight |
| --- | --- |
| Anisic aldehyde | 4.0 |
| Dipropylene glycol | 2.2 |
| Habanolide ®[1)] | 8.0 |
| Hedione ®[2)] | 12.0 |
| Ionone alpha | 20.0 |
| Ionone beta | 40.0 |
| Iso E ®[3)] super | 10.0 |
| Isobornyl acetate | 1.0 |
| 1,3-Benzodioxole-5-carbaldehyde | 2.0 |
| 10%* 2E,6Z-nonadien-i-ol | 0.4 |
| | 99.6 |

*in dipropyleneglycol
[1)]cyclopentadecanolide; origin: Firmenich SA, Geneva, Switzerland
[2)]methyl cis-dihydrojasmonate; origin: Firmenich SA, Geneva, Switzerland
[3)]1-(octahydro-2,3,8,8-tetramethyl-2-naphthalenyl)-1-ethanone; origin: International Flavors & Fragrances, USA The addition of 0.4 parts by weight of 8-propoxyoct-1-en-4-yne to the above-described composition imparted to the latter not only the typical green-violet leaf top note, but also a lively green-fruity-pear and a nice morning dew aspect thanks to its ozone facet.

To the opposite, the addition of 0.4 parts by weight of 7-propoxy-1,3-heptadien-5-yne to the above-described composition showed that the added compound was obviously overdosed and dominating the accord with its green-violet leaf note. This new composition was unbalanced and the nice floral-violet part of the fragrance was hidden by the green top note.

What is claimed is:

1. A perfuming composition comprising
  i) at least one compound of formula

(I)

wherein n represents 1 or 2;
A represents $CH_2$ or CO; and
R represents a $C_{1-4}$ alkyl group, a $C_{1-4}$ alkenyl group or a $C_3$ cycloalkyl group, or when A is a $CH_2$ group, R may also represent a $C_{1-3}$ acyl group,
  ii) at least one ingredient selected from the group consisting of a perfumery carrier and a perfumery base; and
  iii) optionally at least one perfumery adjuvant;
  wherein the compound confers, enhances, improves or modifies violet or violet leaves odor notes of the perfuming composition.

2. The perfuming composition as recited in claim 1, where said compound (I) is a $C_9$-$C_{12}$ compound, or a $C_{10}$-$C_{12}$ compound.

3. The perfuming composition as recited in claim 1, wherein said compound (I) is a compound of formula

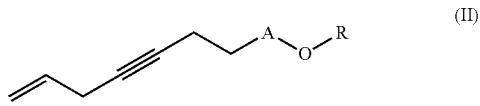

(II)

wherein A represents $CH_2$ or CO and R represents a $C_{1-4}$ alkyl group or a $C_{1-4}$ alkenyl group.

4. The perfuming composition as recited in claim 1, wherein said compound (I) is 8-propoxyoct-1-en-4-yne, 8-methoxyoct-1-en-4-yne or 7-(allyloxy)hept-1-en-4-yne.

5. A perfuming consumer product comprising:
  i) at least one compound of formula

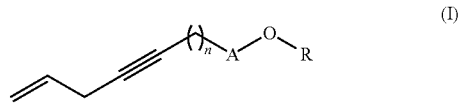

(I)

wherein n represents 1 or 2;
A represents $CH_2$ or CO; and
R represents a $C_{1-4}$ alkyl group, a $C_{1-4}$ alkenyl group or a $C_3$ cycloalkyl group, or when A is a $CH_2$ group, R may also represent a $C_{1-3}$ acyl group, and ii) a perfumery consumer base, wherein the compound confers, enhances, improves or modifies violet or violet leaves odor notes of the perfuming consumer product.

6. A perfuming consumer product according to claim 5, wherein the perfumery consumer base is a perfume, a fabric care product, a body-care product, an air care product or a home care product.

7. A perfuming consumer product according to claim 5, wherein the perfumery consumer base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

8. The perfuming consumer product as recited in claim 5, where said compound (I) is a $C_9$-$C_{12}$ compound, or a $C_{10}$-$C_{12}$ compound.

9. The perfuming consumer product as recited in claim 5, wherein said compound (I) is a compound of formula

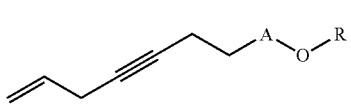

(II)

wherein A represents $CH_2$ or CO and R represents a $C_{1-4}$ alkyl group or a $C_{1-4}$ alkenyl group.

10. The perfuming consumer product as recited in claim 5, wherein said compound (I) is 8-propoxyoct-1-en-4-yne, 8-methoxyoct-1-en-4-yne or 7-(allyloxy)hept-1-en-4-yne.

11. A method to confer, enhance, improve or modify violet or violet leaves odor notes of a perfuming composition that includes a perfume carrier or a perfume base or of a perfumed article, which method comprises adding to said composition or article an effective amount of a perfuming ingredient that is at least a compound of formula:

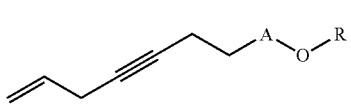

(I)

wherein n represents 1 or 2;
A represents $CH_2$ or CO; and
R represents a $C_{1-4}$ alkyl group, a $C_{1-4}$ alkenyl group or a $C_3$ cycloalkyl group, or when A is a $CH_2$ group, R may also represent a $C_{1-3}$ acyl group;
wherein, in the compound of formula (I), methyl oct-7-en-4-ynoate and 7-ethoxyhept-1-en-4-yne are excluded.

12. The method as recited in claim 11 where said compound (I) is a $C_9$-$C_{12}$ compound, or a $C_{10}$-$C_{12}$ compound.

13. The method as recited in claim 11 wherein said compound (I) is a compound of formula

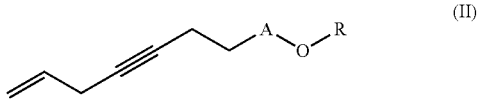

(II)

wherein A represents $CH_2$ or CO and R represents a $C_{1-4}$ alkyl group or a $C_{1-4}$ alkenyl group.

14. The method of claim 11 wherein, in the compound of formula I n is 2, A is CO and R is Cl alkyl.

15. The method of claim 11 wherein the perfuming ingredient is added to a perfuming composition which further comprises:
   i) at least one ingredient selected from the group consisting of a perfumery carrier and a perfumery base; and
   ii) optionally at least one perfumery adjuvant.

16. The method of claim 11 wherein the perfuming ingredient is added to a consumer article which is a perfume, a fabric care product, a body-care product, an air care product or a home care product.

17. The method of claim 16 wherein the consumer article is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

18. A method to confer, enhance, improve or modify violet or violet leaves odor notes of a perfuming composition that includes a perfume carrier or a perfume base or of a perfumed article, which method comprises adding to said composition or article an effective amount of a perfuming ingredient that is at least a compound of 8-propoxyoct-1-en-4-yne, 8-methoxyoct-1-en-4-yne or 7-(allyloxy)hept-1-en-4-yne.

* * * * *